United States Patent
Leonard et al.

(10) Patent No.: US 9,044,578 B2
(45) Date of Patent: *Jun. 2, 2015

(54) LOW PROFILE AGENT DELIVERY PERFUSION CATHETER HAVING A FUNNEL-SHAPED MEMBRANE

(71) Applicant: Abbott Cardiovascular Systems Inc., Santa Clara, CA (US)

(72) Inventors: Michael J. Leonard, Olympia, WA (US); Binh T. Nguyen, Newark, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/062,117

(22) Filed: Oct. 24, 2013

(65) Prior Publication Data

US 2014/0046300 A1    Feb. 13, 2014

Related U.S. Application Data

(63) Continuation of application No. 11/957,237, filed on Dec. 14, 2007, now Pat. No. 8,568,353.

(51) Int. Cl.
*A61M 25/04* (2006.01)
*A61M 31/00* (2006.01)
*A61M 25/00* (2006.01)
*A61M 25/06* (2006.01)

(52) U.S. Cl.
CPC ............ *A61M 25/04* (2013.01); *A61M 25/0026* (2013.01); *A61M 25/0668* (2013.01); *A61M 31/00* (2013.01); *A61M 2025/0004* (2013.01); *A61M 2025/0024* (2013.01); *A61M 2025/0096* (2013.01); *A61M 2025/0681* (2013.01)

(58) Field of Classification Search
CPC ............... A61M 25/04; A61M 31/00; A61M 2025/0004; A61M 2025/0024; A61M 2025/0039; A61M 2025/0096; A61M 2025/0681; A61M 2025/105; A61M 2025/1052; A61M 2025/1084; A61M 2025/1097
USPC ........................ 604/93.01, 104–109
See application file for complete search history.

(56) References Cited

U.S. PATENT DOCUMENTS

| | | |
|---|---|---|
| 5,611,775 A | 3/1997 | Machold et al. |
| 5,769,816 A | 6/1998 | Barbut et al. |
| 2006/0030814 A1 * | 2/2006 | Valencia et al. ........... 604/93.01 |
| 2008/0015569 A1 | 1/2008 | Saadat et al. |

* cited by examiner

*Primary Examiner* — Kami A Bosworth
(74) *Attorney, Agent, or Firm* — Fulwider Patton LLP

(57) ABSTRACT

An agent delivery catheter and method configured to deliver an agent to an inner surface of a patient's body lumen wall by forming a funnel shaped agent containment chamber around at least one portion of the inner surface of the body lumen wall, while minimizing ischemic conditions during the procedure.

10 Claims, 4 Drawing Sheets

LOW PROFILE AGENT DELIVERY PERFUSION CATHETER HAVING A FUNNEL-SHAPED MEMBRANE

CROSS-REFERENCES TO RELATED APPLICATIONS

This application is a continuation of U.S. Ser. No. 11/957,237 filed Dec. 14, 2007, which issued as U.S. Pat. No. 8,568,353 on Oct. 29, 2013, which is incorporated by reference in its entirety. Applicant claims priority to the application in the chain.

BACKGROUND OF THE INVENTION

The present invention relates generally to medical devices, and more particularly to a catheter for delivery of an agent to the coronary or peripheral vasculature.

In the treatment of diseased vasculature, therapeutic agents have commonly been administered, typically as part of other interventional therapies such as angioplasty or stent delivery. Local, as opposed to systemic delivery is a preferred method of treatment in that smaller total levels of medication are administered in comparison to systemic dosages yet are concentrated at a specific site. As a result, local delivery produces fewer side effects and achieves more effective results.

A variety of methods and devices have been proposed for percutaneous drug delivery to a diseased region of the vasculature. For example, catheters having porous balloons can be used to deliver a therapeutic agent infused into the inflatable interior of the porous balloon and through the porous wall of the balloon. Alternatively, prostheses such as stents or other implantable devices provide for local drug delivery when coated or otherwise made to include a therapeutic agent which elutes from the implanted prosthesis. Another suggested method involves the use of one or more catheters having multiple balloons. The diseased region is isolated by inflating the balloons on either side of the diseased region, and the therapeutic agent is infused through a lumen of the catheter shaft and into the isolated diseased region from a delivery port on the catheter shaft located between the balloons. However, the balloons inflated against the vessel wall occlude the vessel, and thus create ischemic conditions there along and distal thereto.

In order to properly position the distal end of a drug delivery catheter in a patient's tortuous distal vasculature, the catheter should preferably have a low-profile, flexible distal section despite also having the necessary structural components required for the drug delivery at the operative distal end of the catheter. One difficulty has been providing for a large amount of drug taken-up and retained at the diseased site, while minimizing the wash out of significant amounts of drug downstream of the treatment site. Drug wash out reduces the efficiency of local intravascular drug delivery, in addition to causing potentially harmful systemic exposure to the drug. Therefore, it would be a significant advance to provide an improved device and method for providing therapy to a desired location within a patient's body lumen.

SUMMARY OF THE INVENTION

The invention is directed to an agent delivery catheter and method configured to deliver an agent to an inner surface of a patient's body lumen wall by forming a funnel shaped agent containment chamber around at least one portion of the inner surface of the body lumen wall, while minimizing ischemic conditions during the procedure.

A catheter of the invention generally includes an elongated shaft having a distal shaft section and an agent delivery lumen which is in fluid communication with an agent delivery distal port in the distal shaft section, a frame fixedly mounted to the distal shaft section which reversibly radially expands from a collapsed to a radially expanded configuration in which the frame expands against the patient's body lumen wall, and which has a proximal end, a distal end, and a radially expandable body section therebetween, and at least one funnel shaped membrane having a mouth secured to the body section of the frame so that the mouth of the membrane reversibly radially expands with the frame away from the shaft as the device is deployed in a patient's body lumen. The membrane has a relatively narrower base (i.e., the base is narrower than the mouth of the membrane) fixedly secured to the shaft at the agent delivery distal port so that the membrane inner surface defines a chamber in fluid communication with the shaft agent delivery lumen, and a longitudinal axis oriented substantially perpendicular to a longitudinal axis of the shaft. As a result, the mouth of the membrane extends around and in contact with only a portion of a circumference of the patient's body lumen wall in the expanded configuration, to thereby expose the portion of the wall to agent delivered from the shaft agent delivery lumen and contained within the chamber of the membrane.

The frame in the expanded configuration has at least one perfusion pathway therethrough, which is outside of the membrane and shaft, and which is configured to allow blood from within the patient's body lumen to flow past the frame (i.e., from proximal of the frame to distal of the frame). Thus, the catheter isolates a region of a blood vessel from blood flow to allow for agent delivery thereto, with continuous perfusion in the blood vessel. The frame typically has two or more funnel shaped membranes circumferentially spaced apart with perfusion pathways therebetween. Depending on the number and configuration of the funnel shaped membranes, the catheter can be configured to simultaneously treat anywhere from nearly all or only a relatively small part of the circumference of the body lumen wall.

A method of the invention generally involves introducing within a patient's body lumen a catheter of the invention, radially expanding the frame against an inner surface of a wall of the patient's body lumen at a desired location in the body lumen to seal the mouth of the membrane(s) against the body lumen wall, and delivering an agent from the agent delivery lumen to a funnel shaped agent containment chamber defined by the membrane with the frame radially expanded against the inner surface of the patient's body lumen wall. The frame is typically a radially self-expanding frame, and is typically collapsed into the deployment sheath or a separate recovery catheter to allow for repositioning or removal of the catheter following the (initial) agent infusion at the desired location in the body lumen.

A catheter of the invention can be used as a stand-alone catheter, or alternatively as a component of a percutaneous delivery system for regional therapy. Additionally, the catheter can be formed by securing the frame/funnel shaped membrane assembly onto a shaft of another device such an embolic protection device, prosthesis delivery device, balloon catheter device, and the like. Therefore, the term "catheter" as used herein should be understood to refer to a variety of the suitable devices configured for percutaneous transluminal procedures.

A variety of suitable agents, including diagnostic and therapeutic agents, can be delivered to the agent containment chamber using the catheter and method of the invention. The agent is typically a therapeutic agent for restenosis, although the agent can be delivered for a variety of treatment procedures, including treatment of a diseased (occluded) blood vessel by delivery of the agent directly into the diseased blood vessel, or treatment of the myocardium of the heart by delivery of an agent into one of the (healthy) coronary arteries. In a presently preferred embodiment, the agent is an anti-inflammatory agent including steroids, or is an agent that induces cholesterol efflux from arterial wall plaque, including PPARα agonists.

A catheter of the invention allows for improved delivery of an agent to a patient's vessel wall, with the agent delivery potentially taking place over an extended period of time, with continuous perfusion provided by the device to thereby avoid disadvantageous, damaging ischemia in the vessel wall. The catheter frame provides for ease of deployment of the operative distal end of the catheter in the patient's body lumen, and avoids damaging the wall of the patient's body lumen. The frame is preferably configured to repeatedly radially expand and collapse in the patient's body lumen, to allow for repositioning of the catheter in the patient's vasculature to treat multiple longitudinally adjacent or spaced apart locations therein. Moreover, depending on the desired use of the catheter, the number and size of funnel shaped membranes can be varied in order to tailor the balance between the competing considerations of agent delivery and perfusion. Additionally, the catheter configuration is well adapted for the treatment of uniform or eccentric body lumens, and for having a working length that is made relatively short for improved device flexibility. The high concentration but low volume agent delivery provided by the catheter avoids potentially harmful systemic release of the agent in the patient's body lumen. These and other advantages of the invention will become more apparent from the following detailed description of the invention and accompanying exemplary drawings.

DETAILED DESCRIPTION OF THE PREFERRED EMBODIMENTS

Figure 1:
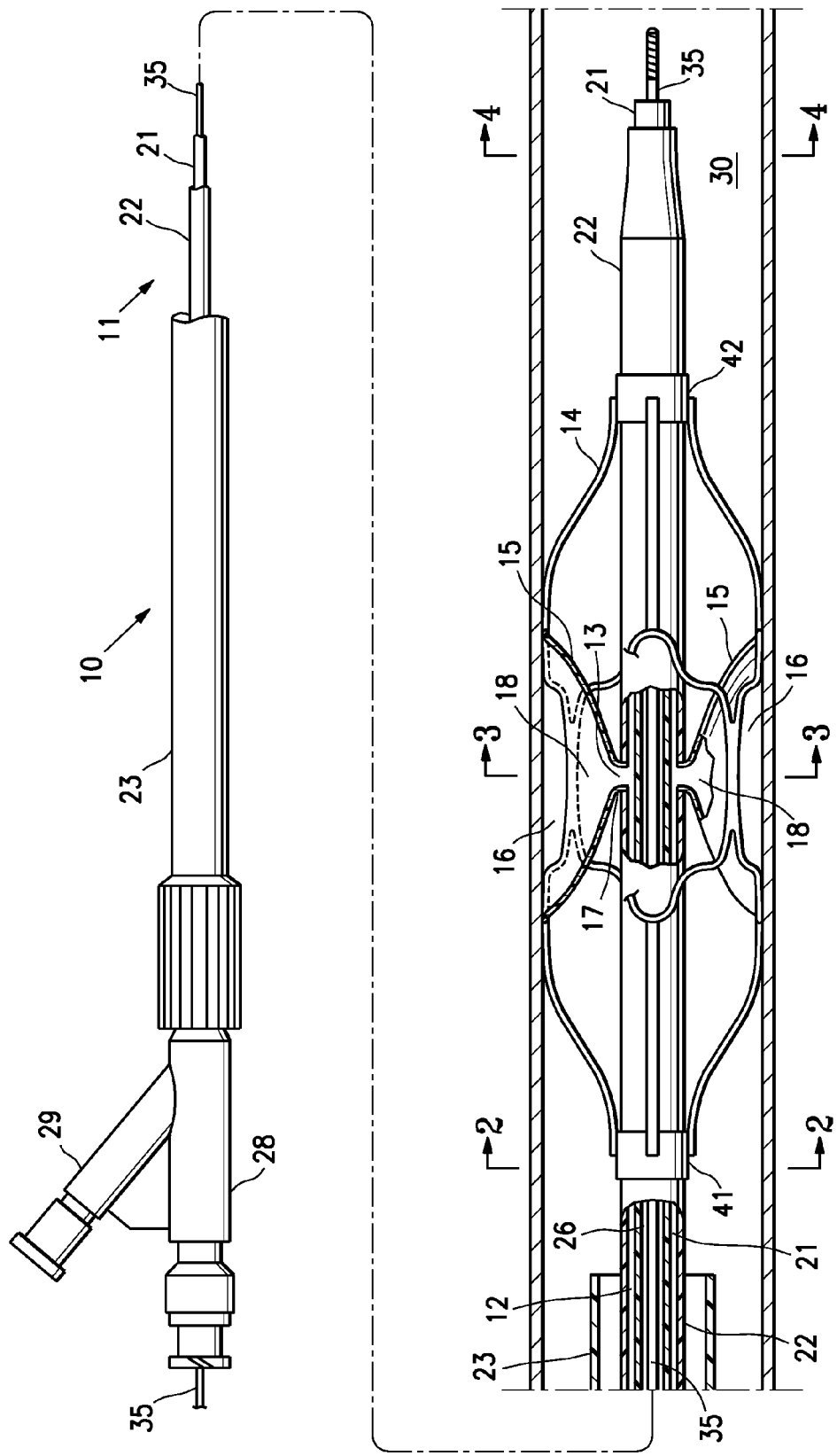
FIG. 1 is an elevational, partially in section, view of an agent delivery perfusion catheter embodying features of the invention, in a patient's body lumen.
Figure 4:
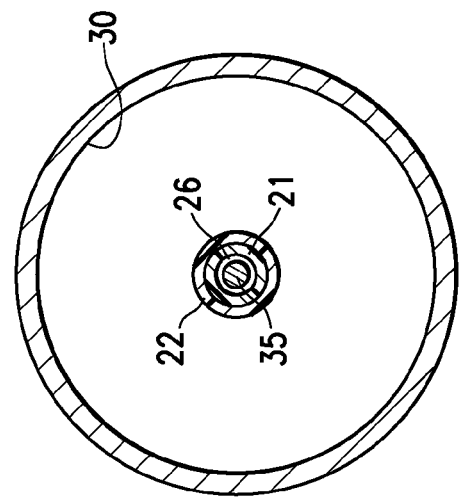
FIGS. 2-4 are transverse cross sections of the catheter of FIG. 1, taken along lines 2-2, 3-3, and 4-4, respectively.
Figure 3:
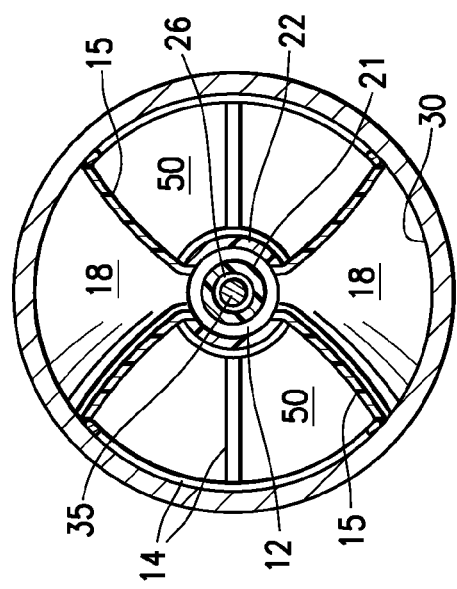
Figure 2:
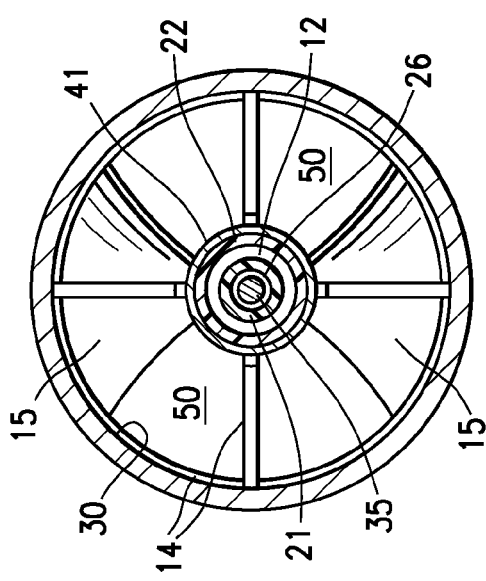

FIG. 1 illustrates an elevational, partially in section, view of an agent delivery perfusion catheter 10 embodying features of the invention, generally comprising an elongated shaft 11 having an agent delivery (infusion) lumen 12 in fluid communication with an agent delivery distal port 13, a frame 14, and funnel shaped membranes 15. The frame 14 reversibly expands from a low profile collapsed configuration to a radially expanded configuration. Each funnel shaped membrane 15 has a mouth 16 secured to the frame, and a base 17 which is narrower than the mouth and which is sealingly secured to the shaft 11 at the port 13. The longitudinal axis of each funnel shaped membrane 15 is oriented substantially perpendicular to a longitudinal axis of the shaft 11 (i.e., preferably perpendicular, or at least more nearly perpendicular than parallel to the underlying shaft longitudinal axis), such that the catheter 10 is configured to deliver an agent to a funnel shaped agent containment 18 chamber defined by the membrane 15 with the frame 14 radially expanded against the inner surface of a wall of a patient's body lumen. FIG. 1 illustrates the frame 14 in the radially expanded configuration in a patient's body lumen 30, and FIGS. 2-3 are transverse cross sections of the catheter of FIG. 1, taken along lines 2-2, 3-3, and 4-4, respectively.

In the illustrated embodiment the shaft 11 comprises an inner tubular member 21, and an outer tubular member 22. An outer deployment sheath member 23 is slidably disposed on the outer tubular member 22. The frame 14 is fixedly secured to the shaft 11 and is configured to radially self-expand to the expanded configuration by release of a radially restraining force, which in the illustrated embodiment is provided by the deployment sheath member 23. Thus, the frame 14 is biased to automatically radially expand to the expanded configuration by slidably displacing the outer tubular member 22 and deployment sheath member 23 relative to one another, such that the frame 14 deploys upon becoming distally spaced from the distal end of the deployment sheath member 23. The frame 14 is typically deployed to the expanded configuration by proximally retracting the deployment sheath member 23 while holding the outer tubular member 22 (and inner tubular member therein) stationary to maintain the position of the frame within the body lumen 30. Although less preferred, due in part to the potential for damage to the vessel wall, the outer member 22 can alternatively or additionally be advanced distally during deployment of the frame 14. The expanded frame 14 will collapse as a tubular sheath is distally advanced over the expanded frame, thus allowing the catheter to be repositioned or removed from the body lumen 30. In one embodiment, the deployment sheath member 23 is configured to also recover the expanded frame by advancing distally over the expanded frame, to thereby re-collapse the frame in the lumen of the deployment sheath member 23 for repositioning or removal of the device 10 from the patient's body lumen. In an alternative embodiment, the deployment sheath member 23 is configured to be peeled or otherwise removed from the outer tubular member 22 of the shaft 11 during deployment of the frame 14, and a separate recovery sheath (not shown) is slidably advanced over the shaft 11 to collapse the frame for recovery. For example, a removable deployment sheath member 23 typically has a weakened wall portion extending along the length thereof, so that as the deployment sheath member 23 is proximally retracted it is caused to peel off the outer tubular member 22 at the proximal end of the catheter 10. The frame 14 can be repeatedly expanded and collapsed to reposition the catheter 10, as for example to treat multiple longitudinal sections of the patient's body lumen wall.

In the illustrated embodiment, the inner tubular member 21 is configured to be slidably advanceable over a guidewire 35 for positioning the catheter 10 in the patient's body lumen 30, such that the inner tubular member 21 has a guidewire lumen 26 separate from the agent delivery lumen 12. The inner tubular member 21 typically tapers to a smaller diameter distal to the frame 14, providing a low profile distal end. In the illustrated embodiment, the agent delivery lumen 12 is the annular space between the inner and outer tubular members 21, 22 of the shaft 11, although alternative shaft designs can be used as are commonly known, including dual lumen extrusions or multiple tubular members defining side-by-side lumens. In one alternative embodiment, the shaft is provided with the general support and pushability required by a fixed core wire with a floppy distal tip, fixed to the shaft inner member 21 from the proximal to the distal end of the shaft inner member 21, to thereby facilitate advancing the catheter 10 in the patient's tortuous vasculature. However, a variety of suitable shaft configurations can alternatively be used which generally provide an agent delivery lumen and an advanceable shaft supporting the frame 14.

A proximal adapter 28 on the proximal end of the catheter 10 provides access to the guidewire lumen 26, and has a port 29 which is in fluid communication with the agent delivery lumen 12 and which is configured for connecting to a fluid agent source (not shown). The adapter can be configured to facilitate displacing the deployment sheath member 23 relative to the outer tubular member 22 to deploy the frame 14 (primarily in embodiments in which the deployment sheath member 23 is not designed to be removed from the inner member 21), similar to conventional adapters or handles on self-expanding embolic protection filters and stent delivery systems.

The frame 14 has a proximal end, a distal end, and a radially expandable body section therebetween. In the illustrated embodiment, the frame has an annular proximal skirt section 41 and distal skirt section 42 mounting the frame on the shaft 11. The frame 14 is typically formed, similar to a self-expanding stent, of a plurality of struts connected such that the frame is reversibly radially expandable. The struts are bonded together or alternatively are an integral, one-piece unit formed for example by cutting out the strut pattern from a tubular member. From the collapsed configuration, the network of struts articulate to expand the tubular body of the frame radially in all directions (i.e., around the entire circumference of the frame) to the expanded diameter. To allow the frame to expand and collapse, one of the annular skirt sections, typically the distal skirt section, is slidably mounted on the shaft (e.g., on the outer tubular member 22), and the opposite end of the frame 14 is fixedly mounted to the shaft 11. Thus, the distal skirt section 42 typically comprises a polymeric or metal ring configured to slide distally on the shaft 11 as the frame 14 radially collapses from the expanded configuration. An alternative embodiment of the frame has a free distal end not mounted on to the shaft, with the free distal end configured to provide a low profile device and to facilitate a desired, uniform radial expansion, with the distal end of the device exerting the force needed to keep the distal seal areas sealed against the body lumen wall. Fixedly securing (i.e., non-moveably bonding) one of the skirt sections of the frame to the shaft can be achieved using a variety of suitable configurations and methods including adhesively bonding the mating surfaces. Although illustrated as a ring member, the skirt sections should be understood to refer to a variety of suitable structural configurations which mount the frame on the shaft, including directly bonding the struts thereto.

In the illustrated embodiment, the struts form four closed loops which have joined edges along the working length section of the frame and which are spaced around the circumference of the frame 14. The closed loops are located between a plurality of longitudinally extending struts extending from the skirt sections to the closed loops of the working length section. Specifically, in the illustrated embodiments, the frame 14 has four longitudinally extending struts at either end of the working length extending from the adjacent skirt section to a curvilinear turn portion of the loop section. However, the frame can have a variety of suitable radially expandable configurations. In the illustrated embodiments, the deployed frame 14 extends fully around the inner circumference of the body lumen 30, as best illustrated in FIGS. 2 and 3. The closed loops of the frame 14 outline the periphery of each membrane mouth 16 secured thereto, such that the mouth 16 of the membrane 15 and its funnel shaped containment chamber 18 in the expanded configuration is unobstructed by the frame 14.

The entire circumference of the mouth 16 of the membrane 15 is bonded to the closed loop struts of the frame, typically by heat bonding, although an adhesive could additionally or alternatively be used. Although not illustrated, in one embodiment, the heat bonding melts the membrane 15 causing it to flow around the struts of the frame and bond to itself, thus encapsulating the struts. The base 17 of the membrane similarly is sealingly secured to the shaft 11 around the port 13 by adhesive or fusion bonding, and optionally with a low profile connector member on the outer surface of the outer tubular member 22 reinforcing the bond, such that the funnel shaped interior chamber 18 defined by the inner surface of the membrane 15 is in fluid communication with the agent delivery lumen 12. The mouth 16 of the membrane is open/spread apart, at least in the radially expanded configuration. The resulting funnel shaped chamber 18 in the membrane is thus an open chamber due to the open mouth 16, unless the mouth 16 is sealed against the inner surface of the wall of the patient's body lumen by the frame in the expanded configuration, as illustrated in FIG. 1.

The mouth 16 of the membrane 15, and the rest of the membrane except for the base 17 secured to the shaft, reversibly radially expands with the frame away from the shaft. Unlike the frame, which radially expands in all directions around the circumference of the shaft, each membrane 15 radially expands in one direction (i.e., on one side of the shaft) away from the shaft 11. The membrane 15 is a polymeric material, and is relatively thin walled and flexible so that it radially expands and collapses readily with the frame. Due to its nature as a membrane, the membrane mouth 16 (oriented in a plane generally parallel to the axis of the shaft 11) is free to actually increase or decrease in diameter as the frame struts articulate during radial expansion or collapse of the frame. In the embodiment of FIG. 1, the membrane mouth 16 will elongate in length as the frame 14 collapses, and will correspondingly increase in width/shorten in length as the frame expands. However, the membrane 15 is preferably formed with the open funnel shape of FIG. 1, to naturally assume the shape in a relaxed state without requiring the membrane to stretch or otherwise distend as the frame radially expands. The generally elliptical membrane mouth 16 is formed in one embodiment (e.g., for a coronary application) with an major dimension of about 5 to about 20 mm and a minor dimension of about 2 to about 6, and an embodiment having a circular membrane mouth 16 has a diameter of about 6 to about 12 mm. The base 17 of the membrane 15 generally has a diameter of about 0.25 to about 1 mm. For coronary use, the axial length of the membrane 15 from the mouth 16 to the base 17 is about 1 to about 3 mm, whereas in peripheral vessels, the length of the membrane 15 is about 1 to about 5 mm, more typically about 2 to about 4 mm. Additionally, for use in peripheral vessels, although the major dimension of the generally elliptical mouth 16 of the membrane would be the same as for coronary applications, the minor dimension of the generally elliptical mouth 16 of the membrane 15 is typically about 6 to about 12 mm. However, a variety of suitable sized membranes are possible depending on the size of the body lumen, the frame, and the desired application.

The membrane 15 is preferably a solid-walled, non-porous polymeric material to contain the agent within the funnel shaped chamber defined by the membrane 15. A variety of suitable polymeric materials can be used to form the membrane 15 including polyurethanes, copolyamides such as polyether block amide (PEBAX) and styrenic block copolymers such as SYNPRENE, and a presently preferred membrane 15 is a polyurethane.

The catheter 10 of FIG. 1 has two funnel shaped membranes 15 on opposite sides of the shaft 11 and frame 14, and each membrane 15 is sealingly secured to the shaft 11 at its own agent delivery port 13 (i.e., the shaft in FIG. 1 has two agent delivery ports 13). The membranes 15 thus provide separate funnel shaped agent containment chambers 18 therein. As best illustrated in FIGS. 2 and 3, the two membranes 15 are circumferentially spaced apart with circumferentially spaced apart perfusion pathways 50 between, in the expanded configuration. The two perfusion pathways 50 are outside of the membrane 15 and shaft 11, and are configured to allow blood from within the patient's body lumen to flow past the frame from the proximal to the distal end of the frame 14 in the expanded configuration. Although the membranes 15 are on opposite sides of the shaft 11 in the embodiment of FIG. 1, the membranes 15 can be at a variety of locations around the shaft including being directly adjacent to one another. Additionally, although the embodiment of FIG. 1 has two membranes 15, a catheter of the invention more generally has one or more membranes 15. Thus, a catheter of the invention can have any number of funnel shaped membranes 15, although the preferred upper limit is about four funnel shaped membranes 15.

Figure 5:
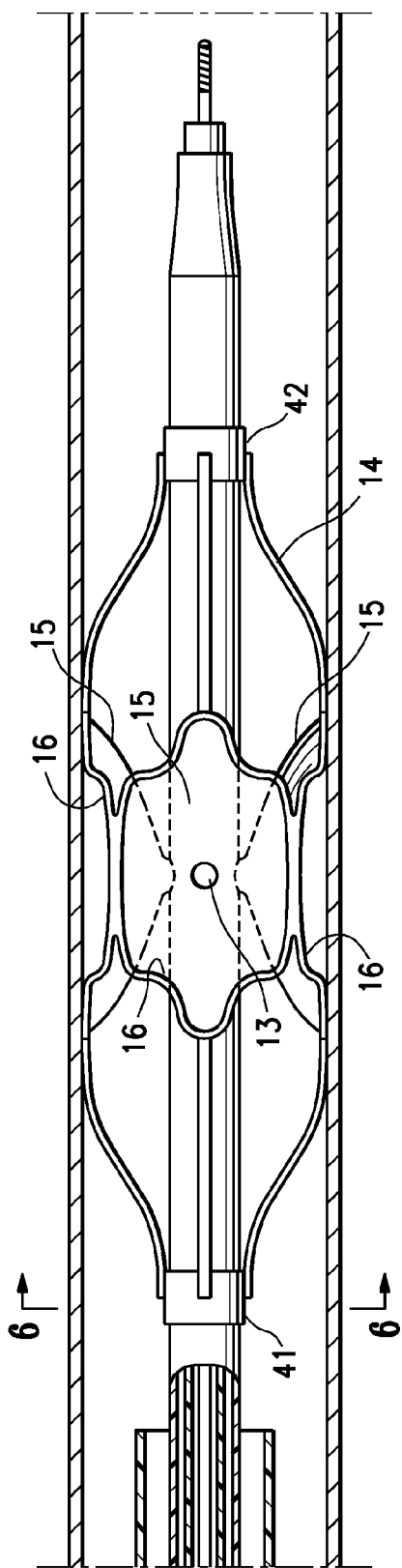
FIG. 5 illustrates an alternative embodiment in which the catheter has four membranes.
Figure 6:
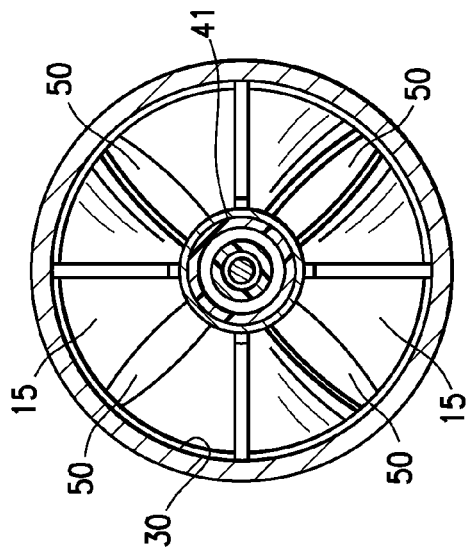
FIG. 6 is a transverse cross section of the catheter of FIG. 5, taken along line 6-6.
Figure 7:
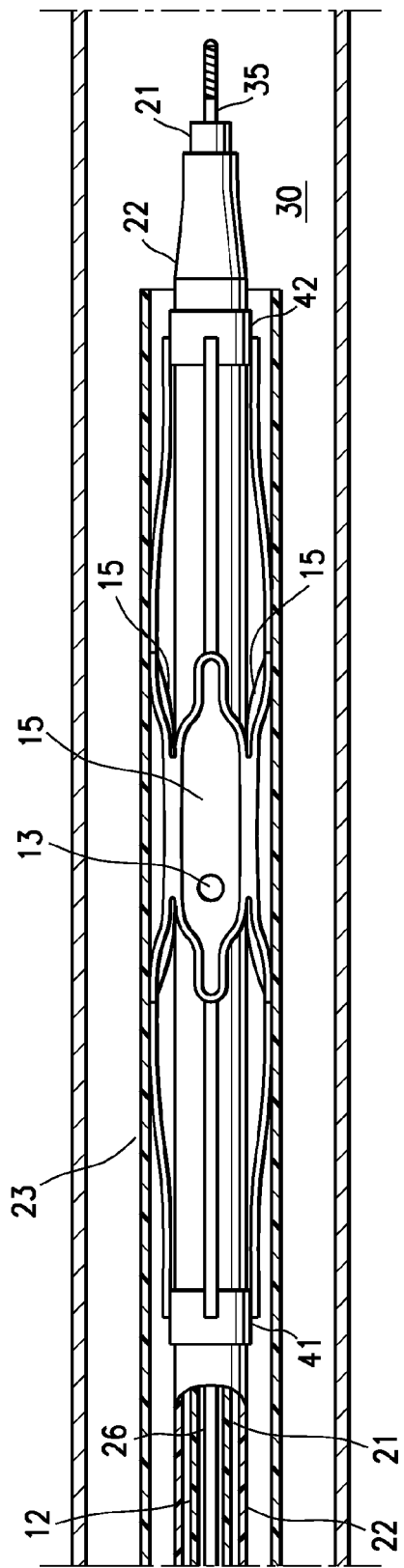
FIG. 7 illustrates the catheter in a collapsed configuration in a sheath.

FIG. 5 illustrates an alternative embodiment in which the frame 14 has four funnel shaped membranes 15 secured to the frame 14. As in the embodiment of FIG. 1, perfusion pathways 50 extend between and are defined in part by the outer surface of adjacent membranes 15, as best shown in FIG. 6 illustrating a transverse cross section of the catheter of FIG. 5, taken along line 6-6. Also like the embodiment of FIG. 1, each of the four funnel shaped membranes is secured to the shaft at its own agent delivery port 13 (the agent delivery port 13 visible in the elevational view of FIG. 5 is surrounded by the membrane which extends out of the page). The four resulting agent containment chambers 18 simultaneously treat a greater area of the body lumen wall than the embodiment of FIG. 1. Where the closed loop sections of the frame 14 are joined together, the mouths 16 of adjacent membranes 15 meet. As a result, the adjacent chambers 18 at the mouths 16 extend nearly around the entire circumference of the body lumen 30 (being separated in the illustrated embodiment by only twice the width of the stent struts). Thus, although each membrane 15 is configured to expose only a portion of the circumference of the patient's body lumen wall to agent, taken together, the four membranes 15 extend fully around the circumference of the frame 14.

However, a tradeoff exists in that the four perfusion pathways 50 (see FIG. 6) between the adjacent membranes 15 in the embodiment of FIG. 5 necessarily provide a smaller total perfusion volume than the two perfusion pathways 50 of the embodiment of FIG. 1. Thus, a catheter of the invention can be specifically tailored for a desired application by varying the number of size of the membranes 15 and the resulting perfusion pathways 50, to provide a specific desired balance between agent treatment and perfusion. For example, a relatively healthy vessel wall which thus requires relatively little drug infusion could potentially be better treated with an embodiment having relatively few or smaller sized membranes 15, due to the larger perfusion pathway volume provided thereby. The catheter typically has two to four membranes 15, which generally provides an acceptable level of both agent delivery and perfusion, and facilitates tightly sealing the mouth of the membranes against the body lumen wall. However, a larger or smaller number of membranes could obviously be used if desired.

Additionally, the catheter 10 can be provided in a range of sizes depending on the patient's body lumen size and intended use of the catheter 10, for example by varying the length or width of the mouth 16 and/or the expanded outer diameter of the frame 14. However, irrespective of the shape and contour of the inner surface of the wall of the patient's body lumen 30, the frame 14 seals the mouths 16 against the wall, including in curved or eccentric, non-circular sections of the patient's body lumen 30. In a presently preferred embodiment, the frame is configured to have a substantially uniform maximum expanded radius around the circumference of the shaft (i.e., the expanded membranes 15 have equal heights), such that the frame 14 can radially expand to generally assume the shape of the wall, whether it is a circular section, or a curved, or non-circular section of the vessel. In a straight, substantially circular section of the body lumen 30, the mouths 16 of the multiple membranes 15 radially expand substantially equal distances from the shaft, and the volume of each funnel shaped containment chamber is substantially equal. In contrast, in a curved or eccentric, non-circular section of the patient's vessel, the frame 14 will radially expand to the non-uniform radius of the body lumen around the circumference of the frame. Thus, the frame 14 is preferably flexible enough to contour to the irregular shape of the vessel, while still providing sufficient radially outward force required for good sealing against the vessel wall. However, the frame 14 could alternatively be configured to have a non-uniform maximum expanded radius around the circumference of the shaft, which is designed specifically for use in a curved or eccentric, non-circular sections of the patient's vessel.

In a method of delivering an agent to the patient's body lumen 30, the catheter 10 is introduced within the patient's body lumen 30. Once the catheter distal section is at the desired location in the body lumen, the frame 14 is radially self-expanded to thereby open and expand the funnel shaped membrane(s) secured thereto. For example, deployment sheath member 23 is preferably proximally retracted while the outer member 22 (an inner member 21 secured therein) is held stationary, to remove the radially restraining force of the deployment sheath member 23 from the frame 14. The deployed frame 14 expands into contact with the wall of the body lumen 30, at least around the mouth 16 of each funnel shaped membrane 15, to exert a force which seals each mouth 16 against the body lumen wall. The frame has a self-expansive force sufficient to fully open the frame to a maximum radially expanded outer diameter of the frame, although the frame 14 is also preferably configured to exert a radial force that does not cause harm or otherwise promote restenosis at the treatment location. Although the membrane 15 can be formed with a smaller height (in a relaxed state) than the expanded frame, such that the wall of the membrane distends or stretches as the frame expands, in a presently preferred embodiment the membrane 15 is instead formed with a height which corresponds to a maximum expanded radius of the frame such that the membrane unfolds/opens away from the shaft as the frame radially expands. An elastic membrane material could be configured to lay down flush with the shaft as the frame collapses, rather than folding. In the expanded configuration, continuous perfusion of the body lumen 30 is provided by the perfusion pathway(s) 50. Thus, blood from within the patient's body lumen flows past the expanded frame 14 from a location proximal of the frame to a location distal of the frame. Because the mouths 16 of the membranes 15 open against the wall of the body lumen 30, and the frame 14 is open-walled and not otherwise covered, nearly all of the body lumen wall is exposed to agent or blood during the procedure. As a result, any disadvantageous ischemic conditions are prevented or inhibited.

In the illustrated embodiments, radially expanding the frame against an inner surface of a wall of the patient's body lumen at a desired location in the body lumen places the mouth 16 of each membrane 15 in contact with, but extending around only a portion of a circumference of, the patient's body lumen wall. With the frame 14 thus deployed in the body lumen 30, agent is introduced into the catheter, so that the agent will absorb into or otherwise treat or act upon the wall of the body lumen 30. Specifically, a source of fluid agent is connected to the port 29 to introduce the agent into the lumen 12, from where it flows through the ports 13 and into each membrane chamber 18. The mouth 16 of the membrane is sealed against the portion of the body lumen wall but is otherwise open, to thereby expose the portion of the wall to agent delivered from the shaft and contained within the chamber of the membrane in the expanded configuration. The catheter 10 is typically configured for delivery of a single agent simultaneously to the multiple funnel shaped containment chambers, although it can alternatively be configured with multiple agent delivery lumens for sequential or simultaneous delivery of one or multiple agents to the different funnel shaped containment chambers if desired. In one embodiment, the agent flow is started before the frame 14 is fully expanded into contact with the vessel wall, in order to flush the funnel shaped membrane 15 with agent (e.g., displace blood/body fluid in the funnel shaped membrane 15 with agent). In an alternative embodiment, the agent flow is started after the frame 14 is fully expanded, to prevent or minimize the systemic release of the agent. The membrane chambers 18 thus allow for high concentration but low volume agent delivery, and avoid systemic release of the agent in the body lumen 30. After the desired agent exposure duration, any remaining agent in the membranes 15 can be removed prior to collapse of the frame 14, by applying a slight vacuum to the agent delivery lumen 12 from the adapter 28.

After a procedure in the patient's body lumen 30, the frame 14 is collapsed in a tubular recovery sheath which is either a separate recovery catheter (not shown) or the deployment sheath member 23. A tubular recovery sheath configured for recovery of the frame 14 has a distal recovery section configured to be slid over the expanded frame in the body lumen. In a presently preferred embodiment, the frame is collapsed by slidably advancing the tubular recovery sheath distally over a proximal portion of the body section of the frame, such that a portion of the frame secured to the mouth 16 of the membrane at least partially collapses before the tubular recovery sheath is distally advanced thereto. Specifically, the longitudinal struts of the expandable body section of the frame 14, which extend from the proximal skirt 41 towards the working length of the frame 14, are first contacted by the tubular recovery sheath and are configured in the expanded configuration to pivot toward the shaft as the tubular recovery sheath is distally advanced thereover, which simultaneously begins to bring the frame at the mouths 16 of the membranes 15 radially inward toward the shaft 11. As a result, bunching or snagging of the membranes 15 in the recovery sheath is prevented or inhibited, to greatly facilitate the rapid and safe recovery of the catheter 10. Thus, the catheter 10 is fully retrievable and allows for extended but temporary drug delivery to an isolated region of the patient's body lumen.

A variety of suitable agents can be delivered using the catheter(s) and method(s) of the invention. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. Suitable therapeutic agents include, but are not limited to, thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. A variety of diagnostic agents can be used according to the present invention. According to the present invention, agents described herein may be provided in a variety of suitable formulations and carriers including liposomes, polymerosomes, nanoparticles, microparticles, lipid/polymer micelles, and complexes of agents with lipid and/or polymers, and the like.

The dimensions of catheter 10 depend upon factors such as the catheter type and the size of the artery or other body lumen through which the catheter must pass. By way of example, the shaft 11 outer tubular member 22 typically has an outer diameter of about 0.022 to about 0.035 inch (0.56 to 0.87 mm), and the deployment sheath member 23 typically has an outer diameter of about 0.060 to about 0.0785 inch (1.5 to 2.0 mm) and a wall thickness of about 0.004 to about 0.008 inch (0.10 to 0.20 mm). The total length of the frame from the proximal to the distal skirt sections is typically about 12 to about 20 mm. Typically, for coronary arteries, the frame radially expands to a maximum outer diameter of about 3.5 to about 4.5 mm. The overall length of the catheter 10 may range from about 100 to about 150 cm, and is typically about 143 cm.

The shaft tubular members can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. A variety of suitable shaft configurations can be used including one or more of the tubular members formed of single or multiple layers or sections of tubing, as are conventionally known for catheter shaft design While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. A catheter for delivering an agent to an inner surface of a patient's body lumen wall, comprising:
   a) an elongated shaft having a distal shaft section and an agent delivery lumen which is in fluid communication with an agent delivery distal port in the distal shaft section;
   b) a frame made from a self-expanding material mounted on the distal shaft section which is biased to expand from a collapsed configuration to an expanded configuration against the patient's body lumen wall, the frame having a loop which remains adjacent to the lumen wall when the frame is in the expanded configuration; and c) an expandable membrane having a mouth secured to the loop of the frame and a base secured to the elongated shaft at the agent delivery distal port so that an inner surface of the membrane defines a chamber in fluid communication with the agent delivery lumen, the mouth of the membrane being movable with the loop when the frame is placed in the expanded configuration such that the mouth of the membrane sealingly engages a portion of the patient's body lumen wall to thereby expose the portion of the wall to agent delivered from the shaft agent delivery lumen and contained within the chamber of the membrane.

2. The catheter of claim 1, wherein the frame in the expanded configuration has at least one perfusion pathway therethrough, which is outside of the expanded membrane and shaft, and which is configured to allow blood from within the patient's body lumen to flow past the frame from a proximal to a distal end of the frame.

3. The catheter of claim 2, having a second expandable membrane having a mouth secured to a second loop of the frame and a base secured to the elongated shaft at a second agent delivery distal port so that an inner surface of the second membrane defines a second chamber in fluid communication with the agent delivery lumen, such that the two chambers formed by the first-mentioned membrane and the second membrane are circumferentially spaced apart from each other to form at least two spaced apart perfusion pathways therebetween in the expanded configuration.

4. The catheter of claim 3, wherein the two expandable membranes are on opposite sides of the shaft.

5. The catheter of claim 1, wherein the shaft includes an outer deployment sheath member having a distally-advanced configuration surrounding and collapsing the frame and a proximally-retracted configuration proximally spaced from at least a section of the frame.

6. The catheter of claim 1, wherein the frame has a plurality of longitudinally extending struts configured in the expanded configuration to pivot toward the shaft as a tubular sheath is distally advanced thereover, such that the frame secured to the mouth of the membrane at least partially collapses before the tubular sheath is distally advanced thereto.

7. The catheter of claim 1, wherein the shaft comprises an outer tubular member with the agent delivery lumen therein and a second lumen for receiving a guide wire lumen therein.

8. A catheter for delivering an agent to an inner surface of a patient's body lumen wall, comprising:
an elongated shaft having a distal shaft section and an agent delivery lumen which is in fluid communication with an agent delivery distal port in the distal shaft section;
a frame made from a self-expanding material mounted on the distal shaft section which is biased to expand from a collapsed configuration to an expanded configuration against the patient's body lumen wall, the frame having a loop which remains adjacent to the lumen wall when the frame is in the expanded configuration;
a first expandable membrane having a mouth secured to the loop of the frame and a base secured to the elongated shaft at the agent delivery distal port so that an inner surface of the membrane defines a chamber in fluid communication with the agent delivery lumen, the mouth of the membrane being movable with the loop when the frame is placed in the expanded configuration such that the mouth of the membrane sealingly engages a portion of the patient's body lumen wall to thereby expose the portion of the wall to agent delivered from the shaft agent delivery lumen and contained within the chamber of the membrane, wherein the frame in the expanded configuration has at least one perfusion pathway therethrough, which is outside of the expanded membrane and shaft, and which is configured to allow blood from within the patient's body lumen to flow past the frame from a proximal end to a distal end of the frame; and
a second, third and fourth expandable membrane, each of the second, third and fourth membranes having a mouth secured to an additional loop formed on the frame and a base secured to the elongated shaft at an additional agent delivery distal port so that an inner surface of each of the second, third and fourth membranes defines a chamber in fluid communication with its respective agent delivery lumen.

9. The catheter of claim 8, wherein the frame has a self-expansive force sufficient to fully open the frame to a maximum radially-expanded outer diameter of the frame.

10. The catheter of claim 8, wherein the frame outlines a periphery of each membrane mouth secured thereto, such that the mouth of each membrane and its chamber is unobstructed by the frame in the expanded configuration.

* * * * *